(12) United States Patent
Neethling et al.

(10) Patent No.: US 11,752,297 B2
(45) Date of Patent: Sep. 12, 2023

(54) STERILIZED PACKAGING SYSTEM FOR CATHETER

(71) Applicant: Anteris Technologies Corporation, Eagan, MN (US)

(72) Inventors: William Morris Leonard Neethling, Booragoon (AU); Christopher P. Olig, Eden Prairie, MN (US); Scott Bliss, Blaine, MN (US); Wayne Paterson, Mendota Heights, MN (US); Philip J. Haarstad, Chanhassen, MN (US); Tuan Doan, Burnsville, MN (US); Alex A. Peterson, Maple Grove, MN (US); David Blaeser, Brooklyn Park, MN (US)

(73) Assignee: Anteris Technologies Corporation, Eagan, MN (US)

( * ) Notice: Subject to any disclaimer, the term of this patent is extended or adjusted under 35 U.S.C. 154(b) by 0 days.

(21) Appl. No.: 17/158,033

(22) Filed: Jan. 26, 2021

(65) Prior Publication Data
US 2021/0146092 A1 May 20, 2021

Related U.S. Application Data

(62) Division of application No. 16/036,417, filed on Jul. 16, 2018, now Pat. No. 10,926,058.
(Continued)

(51) Int. Cl.
*A61M 25/00* (2006.01)
*A61B 50/33* (2016.01)
(Continued)

(52) U.S. Cl.
CPC .......... *A61M 25/002* (2013.01); *A61B 50/20* (2016.02); *A61B 50/30* (2016.02); *A61B 50/33* (2016.02);
(Continued)

(58) Field of Classification Search
CPC .......... A61B 18/1492; A61B 2050/314; A61B 2050/3015; A61B 2050/005;
(Continued)

(56) References Cited

U.S. PATENT DOCUMENTS 3,983,996 A * 10/1976 Hendren, III .......... A61B 50/20
206/583
5,392,918 A 2/1995 Harrison
(Continued)

FOREIGN PATENT DOCUMENTS

CN 103370035 A 10/2013
CN 104093381 A 10/2014
(Continued)

*Primary Examiner* — Rafael A Ortiz
(74) *Attorney, Agent, or Firm* — Fish & Richardson P.C.

(57) ABSTRACT

A packaging system for storing a deployable medical device within a sterilized environment includes a sealed container; a tray disposed within the sealed container; a catheter assembly comprising at least one sheath; a deployable medical device engaged with the catheter assembly; and a sterilizing fluid. The tray comprises a first chamber; a second chamber in fluid communication therewith; and at least a third chamber between the first and second chambers, and in fluid communication with at least the first chamber. The deployable medical device is disposed within the tray in a storage configuration, in which the deployable medical device is disposed within the first chamber in a partially deployed state distally from a distal end of the catheter and the catheter assembly spans between the first chamber and the second chamber. The sterilizing fluid contacts at least a part of the deployable medical device in the storage configuration.

12 Claims, 8 Drawing Sheets

Related U.S. Application Data

(60) Provisional application No. 62/533,429, filed on Jul. 17, 2017.

(51) Int. Cl.
*A61L 2/00* (2006.01)
*A61B 50/30* (2016.01)
*A61B 50/20* (2016.01)
*A61B 18/14* (2006.01)
*A61B 50/00* (2016.01)

(52) U.S. Cl.
CPC ......... *A61L 2/0088* (2013.01); *A61B 18/1492* (2013.01); *A61B 2050/005* (2016.02); *A61B 2050/3008* (2016.02); *A61B 2050/3015* (2016.02); *A61B 2050/314* (2016.02)

(58) Field of Classification Search
CPC . A61B 2050/3008; A61B 50/33; A61B 50/30; A61B 50/20; A61L 2/0088; A61M 25/002
USPC .................. 206/363, 570, 571, 210, 364
See application file for complete search history.

(56) References Cited

U.S. PATENT DOCUMENTS

| | | | |
|---|---|---|---|
| 5,421,334 A | 6/1995 | Jabba | |
| 5,590,778 A | 1/1997 | Dutchik | |
| 6,991,096 B2 | 1/2006 | Gottlieb et al. | |
| 7,578,391 B2 | 8/2009 | Nakamura | |
| 7,712,606 B2 | 5/2010 | Salahieh et al. | |
| 8,123,778 B2 | 2/2012 | Brady et al. | |
| 8,241,319 B2 | 8/2012 | Gilson et al. | |
| 8,747,458 B2 | 6/2014 | Tuval et al. | |
| 8,851,286 B2 | 10/2014 | Chang et al. | |
| 8,997,978 B2 | 4/2015 | Stopek et al. | |
| 9,066,785 B2 | 6/2015 | Tran et al. | |
| 9,155,619 B2 | 10/2015 | Liu et al. | |
| 9,205,172 B2 | 12/2015 | Leonard Neethling et al. | |
| 9,572,653 B2 | 2/2017 | Dardi | |
| 10,758,642 B2 | 9/2020 | Neethling | |
| 2005/0065478 A1 | 3/2005 | Alheidt et al. | |
| 2005/0118056 A1 | 6/2005 | Swanson et al. | |
| 2005/0268573 A1 | 12/2005 | Yan | |
| 2005/0278012 A1* | 12/2005 | Vonderwalde | A61L 2/081 606/108 |
| 2008/0023346 A1 | 1/2008 | Vonderwalde | |
| 2008/0183181 A1 | 7/2008 | Treacy et al. | |
| 2009/0123333 A1 | 5/2009 | Parker et al. | |
| 2009/0194446 A1* | 8/2009 | Miller | A61B 50/30 606/86 R |
| 2011/0290262 A1 | 12/2011 | Tomes et al. | |
| 2012/0103840 A1 | 5/2012 | McCaffrey | |
| 2012/0305441 A1* | 12/2012 | Murray | A61M 25/002 206/363 |
| 2013/0233736 A1 | 9/2013 | Hess et al. | |
| 2016/0287748 A1* | 10/2016 | Neethling | A61L 27/24 |
| 2018/0110578 A1 | 4/2018 | Gallagher | |

FOREIGN PATENT DOCUMENTS

| | | | |
|---|---|---|---|
| CN | 104812439 A | 7/2015 | |
| CN | 105920717 A | 9/2016 | |
| DE | 102007021118 A1 | 11/2008 | |
| JP | 2008-272494 | 11/2008 | |
| WO | 2008/108939 | 9/2008 | |
| WO | 2017040684 A1 | 3/2017 | |
| WO | WO-2017040684 A1 * | 3/2017 | ........... A61F 2/0095 |

* cited by examiner

STERILIZED PACKAGING SYSTEM FOR CATHETER

FIELD OF THE INVENTION

The present disclosure relates to novel and advantageous packaging systems for transportation of a catheter device from a manufacturer to the operating room or other end user.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Catheters are known means for delivering deployable medical devices, such as an imaging system, a stent or other implantable device, through the vasculature, urinary system or peritoneum of the human body. A catheter system generally comprises a handle, often a hub removably connected to the handle, at least one tube having at least one inner lumen, and at least one guidewire disposed within the at least one inner lumen of the at least one tube. A deployable medical device is typically loaded within the catheter prior to the procedure. Some of these deployable medical devices and stents may require them to be stored or transported in an expanded state prior to use so that the devices or stents do not take a permanent shape for an extended time while in a loaded state. In addition to time spent loading the stent, a significant amount of pre-operation time and other resources are spent sterilizing the catheter and the deployable device, separately, in the catherization lab prior to the procedure. For example, in the case of a transcatheter valve replacement, a valve must be rinsed in order to aid the removal of toxic residuals, then crimped and loaded onto the catheter from a distal end of the catheter. It would be desirable to reduce the amount of time and other resources required for these pre-operation procedures by packaging the deployable medical device in at least a partially loaded position on the catheter and within a sterile environment. Thus, a user only has to remove the medical device from the sterilized packaging, without needing to sterilize the components and load the deployable medical device onto the delivery system.

There is a need in the art for packaged, sterilized catheter systems that reduce these preparation steps. U.S. Pat. No. 7,721,606, which is hereby incorporated herein by reference, discusses one sterilized packaging system for an implantable device. As described therein, an implantable device is stored within a wet compartment packaging system while the catheter or delivery device is stored within a necessarily dry compartment of the packaging system. The system here requires a dry compartment completely separate from the wet compartment. The implantable device appears to be delivered into the wet compartment while sheathed, and then the sheath appears to be retracted to dispose the implantable device into the wet compartment filed with a sterilizing fluid. Although this system provides sterilized packaging, it still requires rinsing step to remove any trace of the storage solution from the catheter. It would be desirable to have a packaged, sterilized catheter system that kept the catheter in a sterile environment until use and where a practitioner could remove the catheter from the packaging and use the catheter with little to no additional preparation steps.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure relates to packaging systems for transporting a catheter from a manufacturer in a terminally sterile environment, the catheter having a deployable medical device at least engaged with a distal end of the catheter. In some embodiments, the deployable medical device may be at least partially loaded within the distal end of the catheter. The packaging system comprises a tray disposed within a sealable container, which may be a bag, pouch, vessel, or similar container. The tray may have at least one chamber for holding the catheter and the deployable medical device. In at least one embodiment, the tray comprises at least one chamber for the deployable medical device near a distal end of the tray and at least one chamber for the catheter near a proximal end of the tray. The chambers are within fluid communication with one another so that, in at least one embodiment, the deployable medical device remains wet in a sterilizing or storage fluid. In some embodiments, the entire stored assembly remains wet in a sterilizing or storage fluid. At least the one chamber for the deployable medical device may contain a fluid that is a component of and a final product of a sterilization process, such as, but not limited to, the methods and processes described in U.S. application Ser. No. 15/150,025, entitled "Sterilization Process", which is hereby incorporated by reference herein in its entirety. At least the one chamber for the deployable medical device may contain a sterilizing fluid such as, but not limited to, propylene oxide or 2-Methyloxirane. In at least one embodiment, the sterilizing fluid may comprise a solution of 4%-6% propylene oxide. The deployable medical device is engaged with the catheter in a storage configuration where the deployable medical device is positioned distally from the distal end of the catheter. In at least one embodiment, the deployable medical device is at least partially loaded with the catheter. The deployable medical device and catheter are jointly positioned into the chambers of the tray containing the sterilizing fluid. The tray is then inserted within a sealable container and the container may be sealed. A vacuum pressure may then be applied to remove at least some of the excess air and/or fluid from the chambers of the tray, allowing the deployable medical device and catheter to remain sufficiently wet and therefore in contact with the sterilizing fluid until opened by an end user.

In some embodiments, the packaging system may comprise an attachment feature at a proximal end of the tray for attaching a removable handle to the catheter.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 7 shows a perspective view of one embodiment of the packaging system fully sealed and FIG. 8 shows a perspective view of one embodiment of the tray of the packaging system.

DETAILED DESCRIPTION

The present disclosure relates to packaging systems for a terminally sterilized catheter assembly engaged with a medical device, such as a stent, a transaortic valve replacement device, a transcatheter valve repair or replacement device, systems used for tissue ablation or resection, devices used to deploy cardiac pacing devices, devices used to deploy cardiac sensing devices, devices used to deploy cardiac monitoring devices, devices used to deploy imaging devices, and other suitable devices deployed by a catheter.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Figure 1:
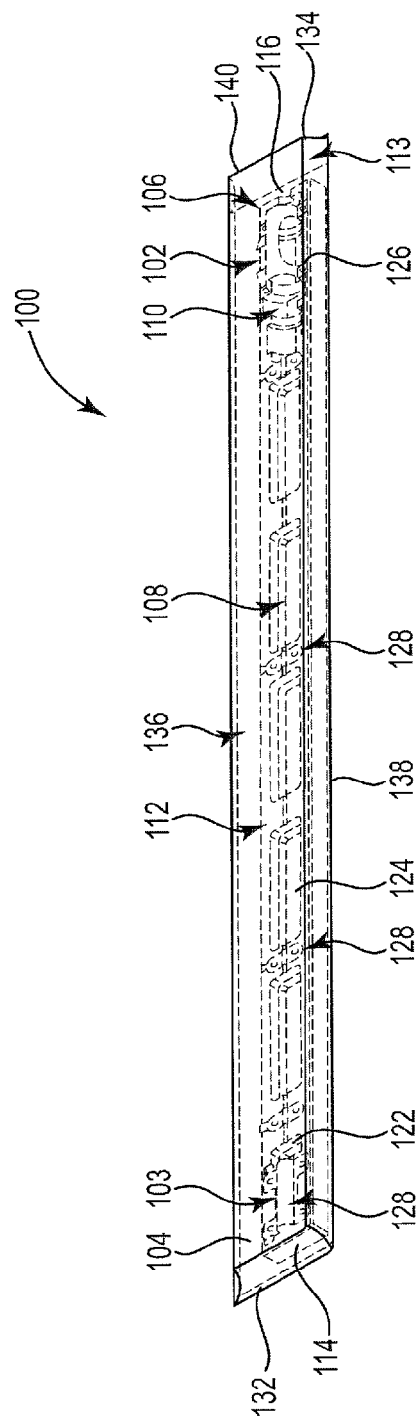
FIG. 1 is a perspective view of a catheter device disposed within the packaging system having a tray and sealable container in an open position, in accordance with one embodiment of the present disclosure.

FIG. 1 shows one embodiment of the packaging system 100 with a terminally sterilized catheter assembly 102 engaged with a deployable medical device 103 at a distal end of the catheter assembly. In some embodiments, at least a portion the deployable medical device 103 may comprise a tissue material or other biomaterial. In some embodiments, the tissue material or biomaterial may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mata, dermal tissue, vascular tissue, cartilage, pericardium, ligament, tendon, blood vessels, umbilical tissue, bone tissue, fasciae, and submucosal tissue and skin. In some embodiments, the tissue material or biomaterial is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. In some embodiments, the deployable device may be a pacemaker, ablation technology, resection devices such as those used for septectomies, and other devices deployable in various systems in the body including but not limited to the cardiovascular system, digestive system, endocrine system, urinary system, reproductive system and respiratory system. The catheter assembly 102 may have a distal end 104 and a proximal end 106. The deployable medical device 103 may be disposed at the distal end 104. The catheter assembly may comprise at least one sheath 108 extending from a position near the distal end 104 to a position near the proximal end 106. The catheter assembly 102 may comprise multiple sheaths, including but not limited to an introducer sheath, an intermediate sheath, retractable sheaths, and other sheaths. The catheter assembly 102 may further comprise a guidewire that, in some embodiments, may extend proximally from the deployable medical device. The catheter assembly 102 may further comprise a handle portion 110 at a proximal end 106.

In at least the embodiment shown, the packaging system 100 comprises a tray 112 capable of receiving the catheter assembly 102 and a sealable container 113 capable of receiving the tray 112. The catheter assembly 102 may be disposed within the tray 112. The tray 112 with the catheter assembly 102 disposed on the tray may be inserted into the sealable container 113. The tray 112 may have a distal end 114 and a proximal end 116. The tray 112 may comprise a plurality of chambers that may contain sterilizing fluid. The plurality of chambers may include, but are not limited to, a first chamber 122 at or substantially near a distal end 114 of the tray 112 for receiving the deployable medical device 103 and at least a second chamber 124 between the first chamber 122 and the proximal end 116. In at least one embodiment, the tray may have a chamber 126 at or substantially near the proximal end 116 of the tray 112 for receiving the handle portion 110 of the catheter assembly. The tray 112 may further comprise retaining features 128 for holding at least a portion of the catheter assembly 102 onto the tray 112 in order to keep the catheter assembly 102 in a desirable position relative to the tray 112. In at least one embodiment, the at least one retaining feature holds the deployable medical device 103, which is at least engaged with the catheter 102 and may be partially loaded within catheter sheath 108, in a desirable position relative to the tray 112. The tray 112 may comprise a polymer material.

One or more of the chambers 122, 124, 126 may contain a volume of a sterilizing fluid such as a sterilant. In some embodiments, the sterilizing fluid may convert to a non-toxic storage solution. In some embodiments, the sterilizing fluid may comprise an initial sterilization solution that converts to a diol over time. In some embodiments, where the device comprises a biomaterial, the fluid may initially comprise a propylene oxide solution that converts to propylene glycol for sterilization and storage of the biomaterial according to the methods and processes described in U.S. application Ser. No. 15/150,025, entitled "Sterilization Process", which is hereby incorporated by reference herein in its entirety. In some embodiments, when the fluid is introduced to the packaging system, it may be introduced as a propylene oxide solution. When the catheter assembly is later removed from the packaging system for use, the fluid may be propylene glycol resulting from the conversion of the propylene oxide solution in the presence of the biomaterial.

The sealable container 113 may have a distal end 132 and a proximal end 134. The sealable container 113 may further comprise a first side wall 136 extending between the distal end 132 and the proximal end 134 and a second side wall 138 extending between the distal end 132 and the proximal end 134. In some embodiments, at least one of the first side wall 136 and the second side wall 138 comprises a transparent material. In at least one embodiment, the sealable container may comprise a polymer. The sealable container may comprise a transparent, nonporous material. In some embodiments, one end of the sealable container 113 is initially closed, and the sealed end, an interior surface of the first side wall 136, and an interior surface of the second side wall 138 may define a chamber 140 of the container. In at least one embodiment, the distal end 132 may be an initially closed end of the container 113 and the proximal end 134 may be an initially open, but sealable end of the container 113. In such an embodiment, the tray 112, with the catheter assembly 102 disposed on the tray 112, may be inserted into the container 113, and more particularly the chamber 140, from the proximal end 134. In at least one other embodiment, the proximal end 134 may be an initially closed end of the container 113 and the distal end 132 may be an initially open, but sealable, end of the container 113. In such an embodiment, the tray 112, with the catheter assembly 102 disposed on the tray 112, may be inserted into the container 113, and more particularly the pouch chamber 140, from the proximal end 134. In some embodiments, once the tray 112 and catheter assembly 102 are fully inserted into the container 113, at least some of the sterilizing fluid may be dispensed into the pouch chamber 140. In other embodiments, once the tray 112 and catheter assembly 102 is at least partially inserted into the container 113, at least some sterilizing fluid may be dispensed into the pouch chamber 140. In some embodiments, at least some the sterilizing fluid may be dispensed into the pouch chamber 140 prior to the tray 112 and catheter assembly 102 being inserted into the container 113. Once the tray 112 is fully inserted into the container 113, the open, sealable end of the container 113 (either proximal end 134 or distal end 132) may be sealed. As shown in FIG. 1, the open, sealable end is the distal end 132 of the sealable container 113. The end may be sealed by using an adhesive, by applying heat, by other mechanical means, and/or combinations thereof. In at least one embodiment, the pouch may have an adhesive strip. In at least one embodiment the pouch may have a flap extending from one of the first wall or the second wall that can be folded over the open end of the pouch. In at least one embodiment, the flap may have at least one adhesive strip at an end of the flap. The flap may further comprise adhesive strips on each edge of the flap such that the flap may be sealed at each exposed edge or end of the flap. In at least one embodiment, the container 113, with the catheter assembly 102 and the tray 112 with the sterilizing fluid all disposed within the container 113, may be inserted into a second sealable container to provide an additional barrier layer. In at least one embodiment, the inner pouch may be sterilized using ethylene oxide or other sterilization methods. Having a dual barrier formed by a first sealable container and a second sealable container allows a non-sterile operator to open the outer second container and a sterile operator to remove the inner first container from the outer second container to open the first container in a fully sterile condition. In this way, there is only a single entry point to the sealable container to remove the sterilized deployable medical device, already operably engaged with the catheter, from the container.

In some embodiments, the outer second container comprises Tyvek® and the sterile inner container may be inserted into the outer container. The outer countainer may sealed and then entire assembly may be sterilized, such as with ethylene oxide.

In at least one embodiment, a method of packaging the catheter assembly 102 with terminal sterilization may comprise disposing the catheter assembly 102 onto the tray 112; inserting the tray 112 into the container 113 at an open end of the container; and sealing the open end of the container 113 either before dispensing a sterilizing fluid, such as but not limited to a sterilant that converts to a non-toxic storage solution, into at least the container 113 or after dispensing the sterilizing fluid into at least one of the container 113 and the tray 112. In at least one embodiment, enough sterilizing fluid must be provided to the tray 112 and/or container 113 to keep the deployable medical device sufficiently wet. In some embodiments, sealing the open end of the container 113 may comprise folding the open end of the container towards the opposite end of the container at least one and applying an adhesive or heat to the container. In some embodiments, the method further comprises affixing, attaching, or otherwise connecting the restraining members to the tray to hold the catheter assembly 102 in proper position relative to the tray. The method may further comprise disposing the sealed container 113 into a second container and sealing an open end of the second container. In at least one embodiment, the sealed end is inserted into the open end of the second container first. In other embodiments, the originally closed end of second container is inserted into the open end of the second container first. In order to remove the catheter assembly 102 from the packaging system 100 for use, the seal of the sealed container may be broken first. In some embodiments, the closed end of the container may be opened first to remove the catheter assembly 102 from the packaging system for use. In at least one embodiment, because the sterilizing fluid converts non-toxic storage solution, no rinsing step, such as rinsing the catheter with an aldehyde solution prior to use, is needed.

Figure 2:
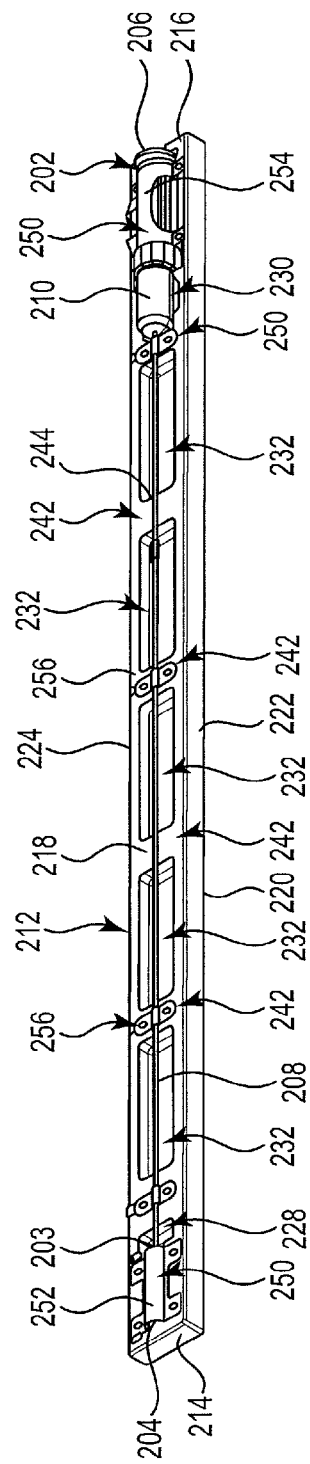
FIG. 2 is a perspective view of a catheter device disposed within the tray of the packaging system, in accordance with one embodiment of the present disclosure.

FIG. 2 shows an embodiment of the tray 212 with the catheter assembly 202 disposed within the tray 212. The catheter assembly 202 may have a distal end 204 and a proximal end 206. The deployable medical device 203 may be disposed at the distal end 204. The catheter assembly may comprise at least one sheath 208 extending from a position near the distal end 204 to a position near the proximal end 206. As shown, the catheter assembly 102 further comprises a handle portion 210 at a proximal end 206. The tray 212 may have a distal end 214 and a proximal end 216. The tray 212 may be generally rectangular in shape as shown FIG. 2, but the tray 212 may have any suitable configuration for retaining the catheter assembly 202 in a suitable position. The tray 212 may comprise a top wall 218, a bottom wall 220, a first side wall 222, and a second side wall 224. The tray 212 may comprise one or more chambers disposed within the top wall 218 of the tray. The tray 212 may comprise a first chamber 228 at or substantially near a distal end 214 of the tray 212 for receiving the deployable medical device 203. The first chamber 228 may be configured to receive the deployable medical device 203. The first chamber 228 may be general rectangular or may have any other configuration. In at least one embodiment, the first chamber 228 may be configured to have a similar size and shape as the deployable medical device and a desired volume for the sterilizing fluid. The tray 212 may, in some embodiments, further comprise a second chamber 230 between the first chamber 228 and the proximal end 216. In at least one embodiment, the second chamber 230 may be configured to receive the handle portion 210. In some embodiments, the second chamber 230 may be a different size and shape than the first chamber 228. In some embodiments, the second chamber 230 may be a groove configured to receive the handle portion 210. The tray 212 may further comprise at least a third chamber 232 between the first chamber 228 and the second chamber 230. In some embodiments, the third chamber 232 may hold some of the sterilizing fluid. As shown in FIG. 2, the tray 212 has five chambers 232 between the first chamber 228 and the second chamber 230. In at least one embodiments, the chamber 232 is smaller relative to at least one of the first chamber 228 and the second chamber 230. In at least one embodiment, the chamber 232 is smaller than the first chamber 228. As shown in FIG. 2, when the catheter assembly is disposed within the tray 212, the sheath 208 may span the length of one or more chambers 232 between the first chamber 228 and the second chamber 230. Between each chamber and an adjacent chamber (for example, between the first chamber 228 and the third chamber 232), the top wall 218 may form a rib portion 242. Each rib portion 242 may further comprise a channel 244 disposed within the top wall 218. The channel 244 may connect one chamber to an adjacent chamber to allow for fluid communication between adjacent chambers (for example, between the chamber 228 and 232). The channel 244 may have a longitudinal axis parallel to a longitudinal axis of the tray 212. Alternatively or additionally, the channel 244 may receive the shaft 208 of the catheter assembly 202. In some embodiments, the chambers 232 may be the same size as the channels 244.

As shown in FIG. 2, a plurality of retaining members 250 are affixed to the tray to keep the catheter assembly 202 in position relative to the tray 212. In at least the embodiment shown, a device retaining member 252 is disposed above the deployable medical device 203 at least partially covering the deployable medical device and the first chamber 228. The device retaining member 252 may be affixed, attached, or otherwise connected to the top wall 218 of the tray 212 as shown. In some embodiments, the device retaining member 252 may be affixed, attached, or otherwise connected to one or more of the side walls 222, 224 or the bottom wall 220. In some embodiments, the retaining member 250 may be tabs formed within the top wall 218 or the side walls 222, 224 for engagement with openings capable of receiving the tabs in the top wall 218 or the side walls 22, 224. In at least the embodiment shown, a handle retaining member 254 is disposed above the handle portion 210 at least partially covering the handle portion 210 and the second chamber 230. The handle retaining member 254 may be affixed, attached, or otherwise connected to the top wall 218 of the tray 212 as shown using any of the means discussed above with respect to the device retaining member 252. In some embodiments, the handle retaining member 254 may be affixed, attached, or otherwise connected to one or more of the side walls 222, 224 or the bottom wall 220. In at least the embodiment shown, a sheath retaining member 256 is disposed above the sheath 208 at the rib portion 242, the sheath retaining member 256 partially covering a portion of the sheath 208. The sheath retaining member 256 may be affixed, attached, or otherwise connected to the top wall 218 of the tray 212 as shown using any of the means discussed above with respect to the device retaining member 252. In some embodiments, the sheath retaining member 256 may be affixed, attached, or otherwise connected to one or more of the side walls 222, 224 or the bottom wall 220.

Figure 3:
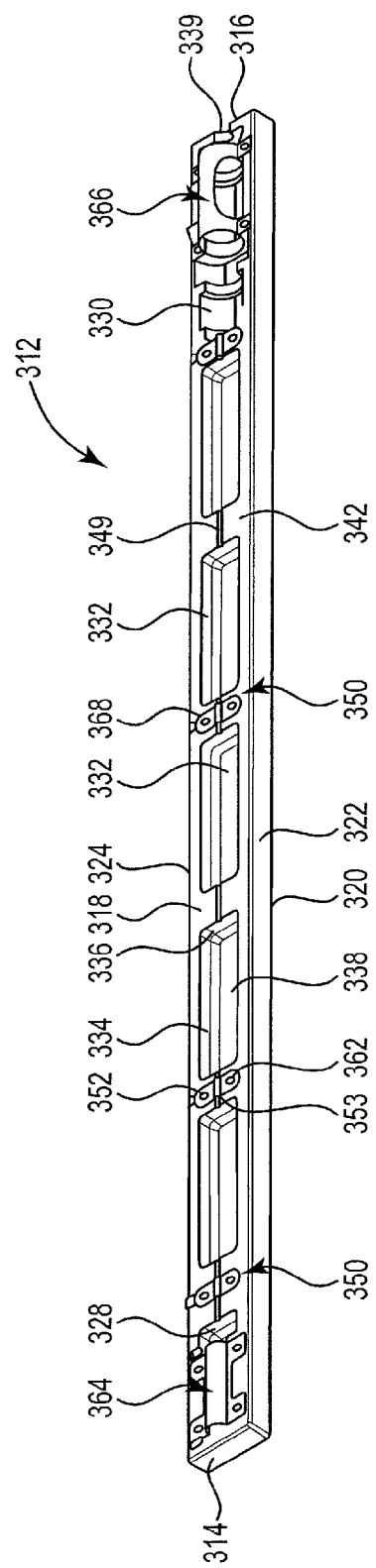
FIG. 3 is a perspective view of the tray of the packaging system, in accordance with one embodiment of the present disclosure.

FIG. 3 shows a tray 312 similar to the tray shown in FIG. 2 but without the catheter assembly. The tray 312 may have a distal end 314 and a proximal end 316. The tray 312 may comprise a top wall 318, a bottom wall 320, a first side wall 322, and a second side wall 324. The tray 312 may comprise a first chamber 328 at or substantially near the distal end 314 of the tray 312 for receiving the deployable medical device, a second chamber 330 near the proximal end 316 for receiving a proximal end of a catheter, and one or more additional chambers 332 between the between the first chamber 328 and the second chamber 330. Each chamber 328, 330, 332 has side walls 334, end walls 336, and a bottom 338. Chambers 328, 330, 332 may each have different depths (in other words, the distance between the top wall 318 and the bottom 338 of the chamber) or they may have the same depth. Chambers 328, 330, 332 may each have different widths (in other words, the distance between side walls 334) and the widths could vary within each chamber, or they may have the same depth. Chambers 328, 330, 332 may each have different lengths (in other words the distance between end walls 336) and the lengths may vary within each chamber, or they may have the same length. In some embodiments, one or more of the chambers 328, 330, 332 may be openings that extend through the entire depth of the tray. In at least the embodiment shown, chamber 330 has a recess 339 at the proximal end 316. In at least one embodiment, the recess 339 may assist in positioning or removing a handle assembly. In at least one embodiment, the recess 339 may align with a port on the exterior container to improve fluid flow of the sterilizing fluid entering the container. Between each chamber and an adjacent chamber, the top wall 318 may form a rib portion 342. Each rib portion 342 may further comprise a channel 344 disposed within the top wall 318 for at least one of fluid communication between adjacent chambers and receiving the sheath of the catheter device. The channel 344 may have at least a bottom surface 346. In at least one embodiment, the channel 344 may be more shallow than each of the adjacent chambers. In other words, the channel 344 may have a depth at its lowest point that is less than a depth of either of the adjacent chambers 328, 330 as shown in FIG. 3. The channel 344 may have at least a bottom surface that is rounded for receiving the sheath, however the bottom surface may in other embodiments be angled, flat or otherwise configured.

FIG. 3 further shows a plurality of retaining members 350 affixed to the tray 312. In at least the embodiment shown, each retaining member 350 has a top surface 352, a bottom surface 353, a proximal end 354, a distal end 355, a first side 356 and a second side 357. In at least the embodiment shown, each retaining member 350 has a curved top surface 352 and a curved bottom surface 353, although other configurations are contemplated by this invention. Each retaining member 350 has an attachment feature 362 configured for connecting to a mating feature on the tray 312. In at least the embodiment shown, a device retaining member 364 is disposed above the first chamber 328. In at least the embodiment shown, a handle retaining member 366 is disposed above the second chamber 330. One or more sheath retaining members 368 may be disposed above the channel 344. The retaining members 350 assist with maintaining the catheter assembly in position relative to the tray 312.

Figure 4:
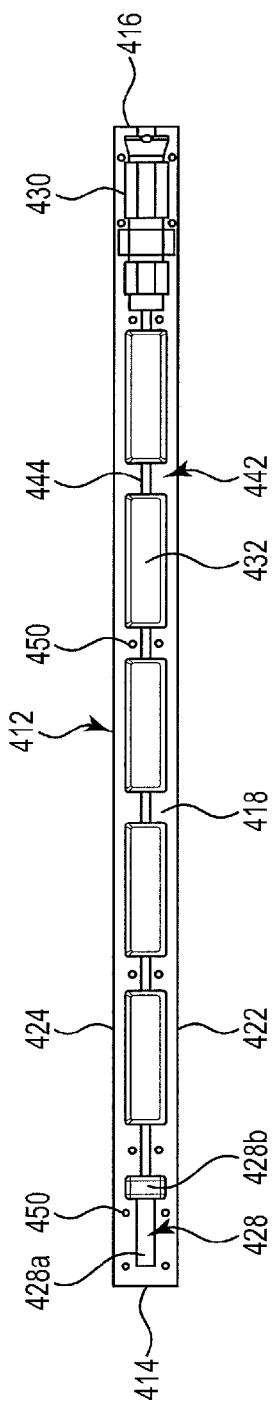
FIG. 4 is a top view of the tray, in accordance with one embodiment of the present disclosure.

FIG. 4 shows a top view of the tray 412 similar to the trays shown in FIGS. 2-3 without a catheter device disposed within the tray 412 and without any retaining members. The tray 412 may have a distal end 414 and a proximal end 416.

The tray 412 may comprise a top wall 418, a bottom wall (not shown), a first side wall 422, and a second side wall 424. The tray 412 may comprise a first chamber 428 at or substantially near the distal end 414 of the tray 412 for receiving the deployable medical device, a second chamber 430 near the proximal end 416 for receiving the handle portion, and one or more additional chambers 432 between the between the first chamber 428 and the second chamber 430. As shown in FIG. 4, first chamber 428 may have first portion 428a and second portion 428b, where second portion 428b has a different configuration than first portion 428a. Between each chamber and an adjacent chamber, the top wall 418 may form a rib portion 442. Each rib portion 442 may further comprise a channel 444 disposed within the top wall 418 for at least one of fluid communication between adjacent chambers and receiving the sheath of the catheter device. The tray 412 further comprises attachment features 450 for connecting with the attachment features on the retaining members described above, which may be disposed within each rib portion 442 or on the top wall 418. The attachment features 450 may be indentations in the top wall 418 that may be round, square, rectangular, polygonal or have other configurations for a press fit connection to corresponding attachment features on the respective retaining members.

Figure 5:
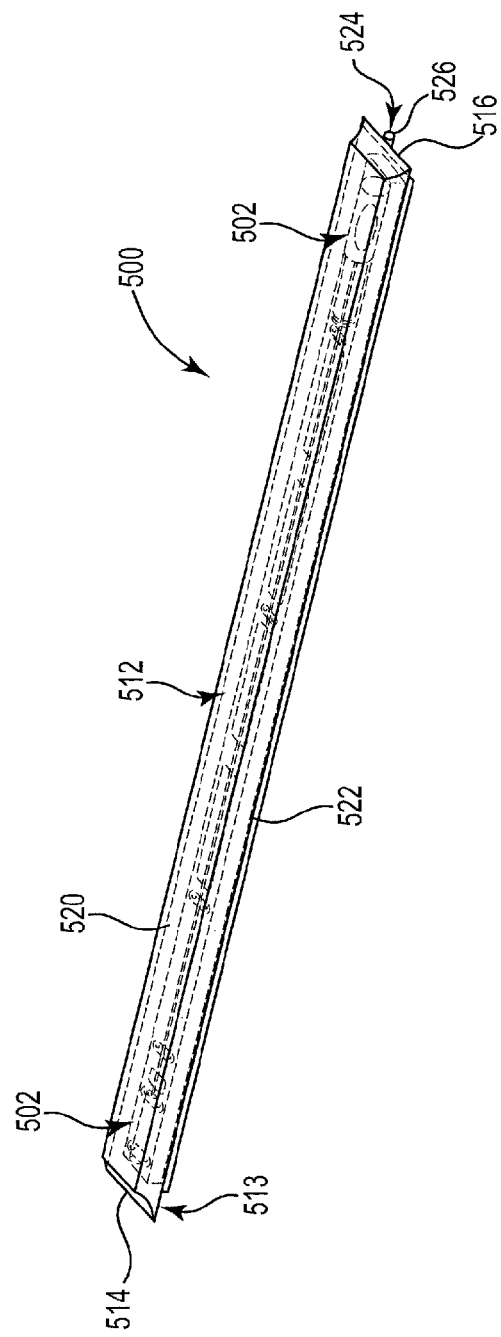
FIG. 5 is a perspective view of the packaging system, in accordance with one embodiment of the present disclosure, with the sealable container in a closed position.

In some embodiments of the packaging system, such as the embodiment 500 shown in FIG. 5, the packaging system may comprise a tray 512 disposed within a sealable container 513 having a distal end 514, a proximal end 516, a first side wall 520, and a second side wall 522. The sealable container 513 may further comprise at least one spout 524, which may be disposed as shown in FIG. 5 at a proximal end 516 of the container. The at least one spout 524 may be disposed at a distal end 514 of the container, on the first side wall 520 of the container, or the second side wall 522 of the container. The spout may be used to insert fluid into a sealed container, or to remove air and/or fluid from a sealed container. FIG. 5 shows a catheter assembly 502 disposed within the container and the packaging system in a closed and sealed position. In at least one embodiment, the tray 512 may be inserted into the sealable container 513 from an open end of the container. Where the spout 524 is positioned at an end 514, 516, the tray 512 is inserted from an end opposite of the end where the spout 524 is located. The open end of the container 513 can then be sealed by applying heat, using adhesive, or other sealing means. The sterilizing fluid can then be disposed into the container chamber through the spout 524 by connecting the spout 524 to a sterilizing fluid dispenser. Excess air and/or liquid can be removed from the container through the spout 524 or through another pout on the sealable container, if more than one spout is provided. In at least one embodiment, a cap 526 is placed on each of the at least one spouts 524 to finally seal the packaging system.

In some embodiments, a process for sterilizing a catheter assembly may comprise inserting the catheter assembly disposed within the tray into the sealable container, which may or may not already include a volume of the sterilizing fluid. Where the catheter assembly and the tray are inserted into a "dry" sealable container, the sterilizing fluid may be disposed into the sealable container, either through an open end of the sealable container or through the spout. The sealable container may then be sealed by sealing the open end of the sealable container or sealably closing the spout with a cap. In some embodiments, vacuum pressure may be applied prior to fully sealing the sealable container to remove some or all of the excess air or some excess fluid from the sealable container. Once sealed, the sterilizing fluid proceeds to sterilize the catheter assembly within the sealable container for a sterilization period. In some embodiments, once fully sealed, the packaging system may be rotated or otherwise agitated during the sterilization period. The packaging system may be rotated in a first direction about the longitudinal axis of the packaging system. In some embodiments, the packaging system may also be rotated in a second direction about the longitudinal axis of the packaging system. In still other embodiments, the packaging system may be rotated in the first direction and then in the second direction and alternate between these two directions to agitate the packaging system. In some embodiments, the packaging system may be agitated in an agitator where a first end of the packaging system is moved to a position higher than a second end opposite the first of the packaging system and then the second end is moved to a position higher than the first end, so the fluid moves within the assembly from end to end. This agitation step helps move any small air bubbles that may be present within the catheter and helps assist the sterilizing fluid to contact the surfaces of the catheter, and more particularly the catheter lumen.

In at least one embodiment, after the sterilization period has ended and the sterilizing fluid has converted into a storage solution, at least a portion of one end of the sealed container may be unsealed, either by cutting or otherwise removing a portion of the seal to create an opening within the sealed container. At least some of the storage solution may be drained from the sealed container through the opening. In at least one embodiment, the storage solution is aseptically drained from the container. This creates a vacuum within the container. The opening can then be resealed prior to use.

Figure 6:
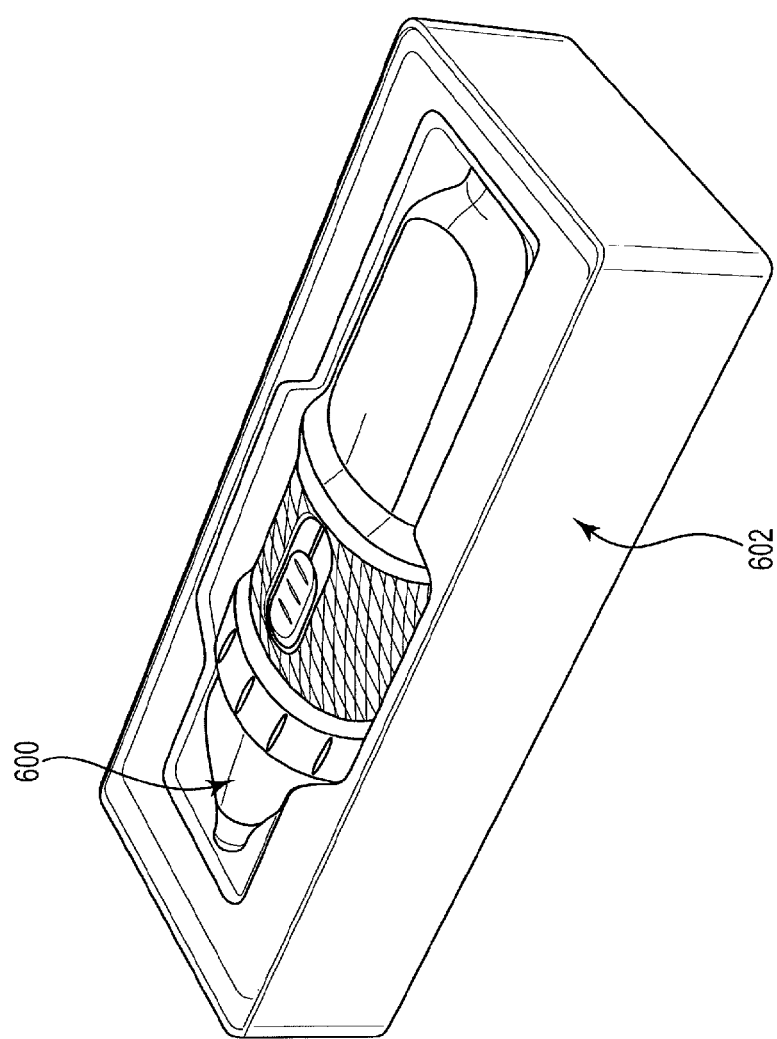
FIG. 6 shows a view of a removable handle, in accordance with one embodiment of the present disclosure.

In at least some embodiments, the packaging system may be used with a catheter assembly that has a removable handle. In such embodiments, the packaged catheter assembly may include only the guidewire, deployable device, and the sheath or sheaths required for deployment. The catheter assembly may have a handle attachment feature at a proximal end of one sheath. In at least one embodiment, the catheter assembly may comprise a safety lock between the deployable device and the handle attachment feature a proximal end of the sheath that prevents deployment in order to keep the deployable device positioned in a partially deployed state. This catheter assembly may then be disposed within a tray that has a chamber for the deployable medical device and a chamber for receiving the safety lock. The handle may have a snap attachment feature for mating with the handle attachment feature. The snap attachment feature comprises a flanged end for mating and a control tube that is rotatable relative to the handle knob. The snap attachment feature has a deployment safety lock, which can be removed once its connected to the catheter. Handle knob can be rotated. Reversing the direction of the knob then retracts the control tube and you can deploy the valve. In some embodiments, the handle may be connected to the handle attachment feature while the deployable device remains in the package. In some embodiments, the handle may be connected to the attachment feature once the deployable device is removed from the packaging in a sterile environment. In some embodiments, such as the embodiment shown in FIG. 6, the removable handle 600 may be separately packaged within a sealed container 602. The sealed container 602 may be hermetically sealed or otherwise sealed. The sealed container 602 may include a sterilizing fluid, or it may be just vacuum sealed in air. Once the practitioner is ready to use the catheter and the handle, the sealed container 602 with the handle may be opened and the packaging system with the catheter assembly may be opened and the removable handle 600 may be attached to the proximal end of the catheter assembly. In at least one embodiment, the removable handle 600 may be sterilized after a procedure, sealed in a sealed container, and reused.

Figure 7:
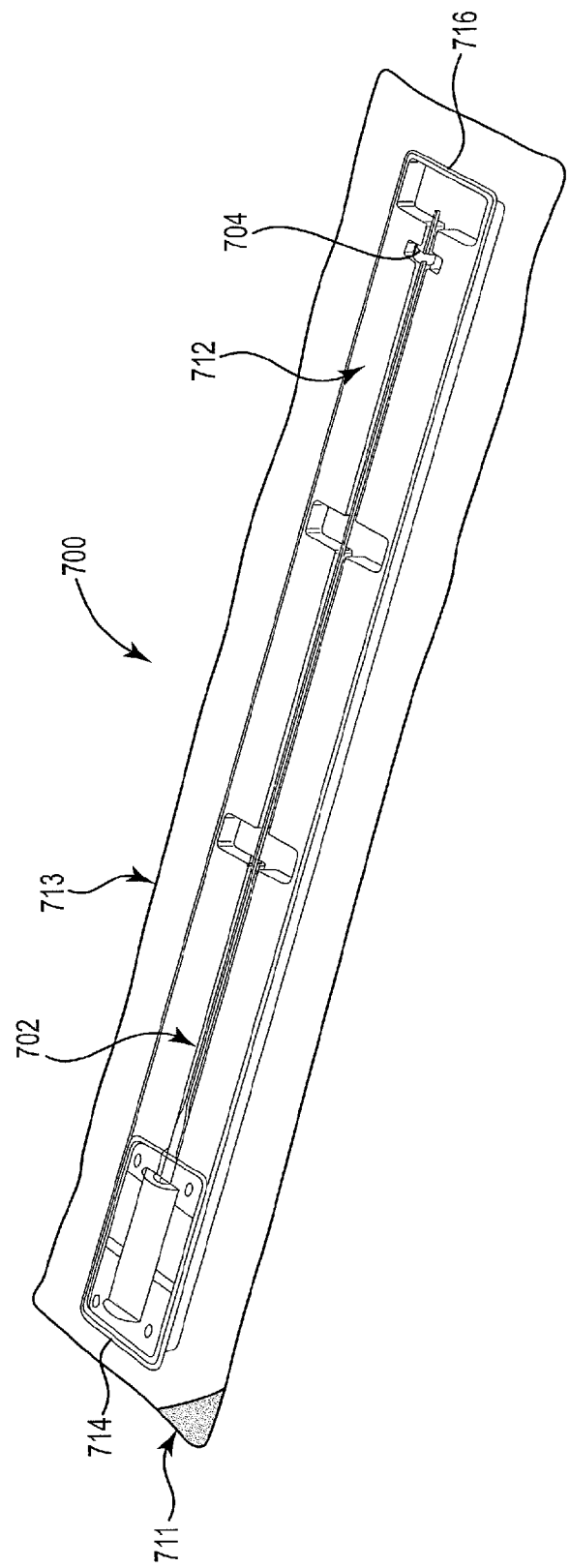
FIGS. 7-8 show perspective views of the packaging system, in accordance with one embodiment of the present disclosure.
Figure 8:
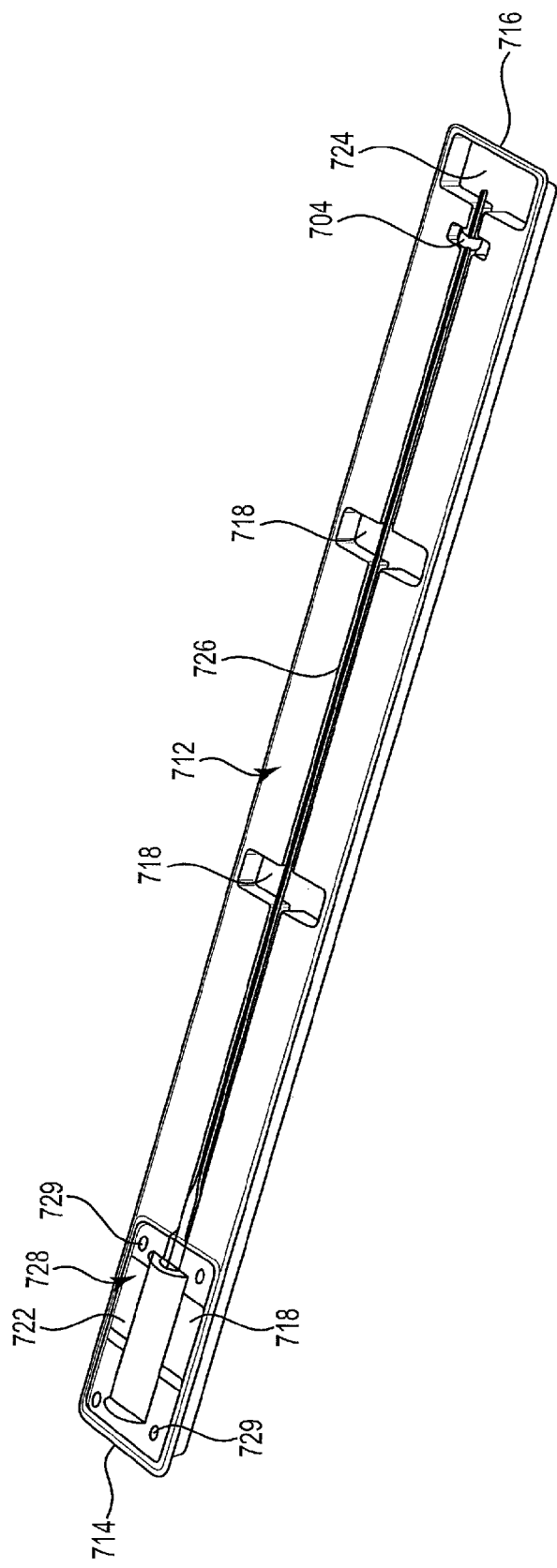

FIGS. 7-8 show another embodiment of the packaging system 700 with a terminally sterilized catheter assembly 702 engaged with a deployable medical device at a distal end. The catheter assembly 702 may further comprise a handle attachment feature 704 for connecting the proximal end of the catheter assembly 702 with a removable handle, such as the removable handle shown in FIG. 6. In at least the embodiment shown in FIGS. 7-8, the packaging system 700 comprises a tray 712 capable of receiving the catheter assembly 702 and a sealable container 713 capable of receiving the tray 712. As shown in FIG. 7, the catheter assembly 702 is disposed within the tray 712, and the tray 712 is disposed within the sealable container 713. The sealable container 713, in the embodiment shown, has a tab 711 near an end of the sealable container 713 which can be pulled to separate it from the rest of the sealable container 713 and open the container. In at least one embodiment, the tab 711 is at a distal end of the sealable container 713 and in other embodiments the tab 711 may be at a proximal end. In some embodiments, the sealable container may have multiple tabs 711. FIG. 8 shows the tray 712 removed from the sealable container 713. The tray 712 may have a distal end 714 and a proximal end 716. The tray 712 may comprise a plurality of chambers 718 that may contain sterilizing fluid. The plurality of chambers 718 may include, but are not limited to, a first chamber 722 at or substantially near a distal end 714 of the tray 712 for receiving the deployable medical device 703 and at least a second chamber 724 between the first chamber 722 and the proximal end 716. The tray 712 may have a plurality of chambers 718 between the first chamber 722 and the second chamber 724. The chambers 718 are connected to one another by channel 726 and the chambers 718 may be in fluid communication with one another through the channel 726. In at least one embodiment, a portion of the catheter assembly 702 rests within the channel 726. The tray 712 may further comprise a device cover 728 that provides some additional protection to the deployable medical device 703, especially where the device comprises tissue. The device cover 728 may be retained on the tray 712 with several attachment features 729 on the tray that may, in some embodiments, mate with corresponding attachment features on the device cover 728. In some embodiments the attachment features 729 may comprise glue or another adhesive to removably connect the device cover 728 to the tray 712. The device cover 728 may be sized to fully, or at least substantially, overlap the first chamber 722. The device cover 728 may comprise a transparent material such that the deployable medical device 703 may be observed while the deployable medical device is still stored within the tray.

Although the above description and figures discusses embodiments of the invention of the present disclosure according to generally a tray disposed within a container, other packaging systems of the present disclosure using a sterilizing fluid such as, but not limited to, a sterilant that converts to a non-toxic storage solution are contemplated by this invention. In at least one embodiment, a flat card may be provided with retaining features for holding the catheter and the deployable medical device in a desired position. The flat card may be inserted into a container. In one embodiment, a plastic or glass vessel with a removable cap at a proximal end of the vessel may be provided. An interior surface of the vessel may define a chamber for receiving the sterilizing fluid and the deployable medical device, which is operably engaged with at least one shaft of a catheter. In some embodiments, the chamber may further receive a catheter handle. In some embodiments, the removable cap may have a sealed opening where the handle may be attached to the catheter shaft at a proximal end of the distal cap. In some embodiments, the vessel may be a flexible, but sufficiently rigid, plastic tube with foam members that assist with retaining the deployable medical device in a desired position. Caps at one or both ends may be mechanically sealed or adhesively sealed. In one or more embodiments, at least one of the caps may have a port for dispensing the sterilizing fluid into the vessel. In another embodiment, the tray may have a cover pivotably attached to the tray so that the tray forms a clamshell-type packaging for the deployable medical device. When the cover is in an open position relative to the tray, the deployable medical device and at least the catheter shaft may be inserted into the tray. In at least one embodiment, the catheter handle may also be inserted into the tray. The cover may then be pivoted into a closed position relative to the tray and sealed along all unattached exterior edges of the tray where the cover is adjacent to the tray. In some embodiments, the sterilizing fluid may be dispensed into chambers of the tray prior to the cover being closed and sealed. At least one of the cover and the tray may include an opening for delivery of the sterilizing fluid to at least one chamber of the tray. In at least one embodiment, the cover may be separate from the tray, rather than pivotably connected to the tray. In such embodiments, the cover may be positioned onto the tray in a closed position and sealed along all unattached exterior edges of the tray where the cover is adjacent to the tray.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or"

refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the customized urn. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A packaging system for storing a deployable medical device within a sterilized environment, the packaging system comprising:
   a sealed container with at least one sealed seam;
   a tray disposed within the sealed container, the tray having a first end, a second end, a top wall, and a bottom wall, the tray comprising:
      a first chamber near the first end;
      a second chamber near the second end in fluid communication with the first chamber;
      at least a third chamber positioned between the first chamber and the second chamber, the third chamber in fluid communication with the first chamber and the second chamber;
      a first rib portion in the top wall between the first chamber and the third chamber, the first rib portion comprising a first channel extending between the first chamber and the third chamber;
      a fourth chamber positioned between the second chamber and the third chamber, the fourth chamber in fluid communication with the first chamber, the second chamber, and the third chamber; and
      a second rib portion in the top wall between the second chamber and the fourth chamber, the second rib portion comprising a second channel extending between the second chamber and the fourth chamber;
   a catheter assembly having a distal end and a proximal end, the catheter assembly comprising at least one sheath and spanning between the first chamber and the second chamber;
   a deployable medical device comprising a tissue material, the deployable medical device engaged with the catheter assembly and disposed within the tray in a storage configuration, wherein in the storage configuration, the deployable medical device is disposed within the first chamber in a partially deployed state distally from a distal end of the catheter assembly; and
   a sterilizing fluid disposed within at least the first chamber, wherein the sterilizing fluid contacts at least a part of the deployable medical device in the storage configuration, and wherein each of the first chamber, second chamber, third chamber, and fourth chamber contain a volume of the sterilizing fluid.

2. The packaging system of claim 1 wherein the tray further comprises an attachment means at the second end of the tray for attaching a removable handle to the catheter assembly.

3. The packaging system of claim 1, wherein the tissue material is in contact with the sterilizing fluid while the deployable medical device is in the storage configuration.

4. The packaging system of claim 1, further comprising a device retaining member attached to the tray and positioned over the deployable medical device to retain the deployable medical device within the first chamber.

5. The packaging system of claim 4, wherein the device retaining member is positioned between the tray and the sealed container, and the device retaining member has a curved top surface and a curved bottom surface.

6. The packaging system of claim 1, further comprising at least one catheter retaining member attached to the tray and positioned over a portion of the sheath of the catheter assembly to retain the catheter assembly relative to the tray.

7. The packaging system of claim 6, wherein the at least one catheter retaining member is positioned between the tray and the sealed container, and the at least one catheter retaining member has a curved top surface and a curved bottom surface.

8. A packaging tray for storing a deployable medical device and a catheter assembly engaged with the deployable medical device in a sterilizing fluid in a container, the packaging tray comprising:
   a first end and a second end;
   a top wall and a bottom wall;
   a first chamber near the first end configured to receive the sterilizing fluid and the deployable medical device, wherein the deployable medical device comprises a tissue material;
   a second chamber near the second end in fluid communication with the first chamber;
   a third chamber positioned between the first chamber and the second chamber, the third chamber in fluid communication with the first chamber,
   a first rib portion in the top wall between the first chamber and the third chamber, the first rib portion comprising a first channel extending between the first chamber and the third chamber;
   a fourth chamber positioned between the second chamber and the third chamber, the fourth chamber in fluid communication with the first chamber, the second chamber, and the third chamber; and
   a second rib portion in the top wall between the second chamber and the fourth chamber, the second rib portion comprising a second channel extending between the second chamber and the fourth chamber.

9. The packaging tray of claim 8, further comprising:
a recess at the second end.

10. The packaging tray of claim 8, further comprising:
a device retaining member disposed over at least a portion of the first chamber and attached to the top wall, wherein the device retaining member has a curved top surface and a curved bottom surface.

11. The packaging tray of claim 10, further comprising a sheath retaining member attached to top wall at the first rib portion, the sheath retaining member extending over the first channel.

12. The packaging tray of claim 11, wherein the sheath retaining member has a curved top surface and a curved bottom surface.

* * * * *